United States Patent [19]

Söderberg

[11] Patent Number: 5,004,420

[45] Date of Patent: Apr. 2, 1991

[54] DENTAL BRIDGE AND MANNER FOR PREPARATION

[75] Inventor: Per O. Söderberg, Stockholm, Sweden

[73] Assignee: Astra Meditec Aktiebolag, Mölndal, Sweden

[21] Appl. No.: 183,891

[22] Filed: Apr. 20, 1988

[30] Foreign Application Priority Data

Apr. 22, 1987 [SE] Sweden ............................. 8701653

[51] Int. Cl.⁵ ............................................. A61C 13/12
[52] U.S. Cl. .................................. 433/172; 433/200.1
[58] Field of Search ................. 433/200.1, 221, 222, 433/172, 173, 174, 175, 176, 192, 195, 206, 207, 208, 209, 210

[56] References Cited

U.S. PATENT DOCUMENTS

| | | | |
|---|---|---|---|
| 360,206 | 3/1887 | Colomb | 433/221 |
| 4,085,506 | 4/1978 | Lew | 433/172 |
| 4,488,940 | 12/1984 | Wismann | 204/4 |
| 4,689,013 | 8/1987 | Lustig | 433/192 |
| 4,744,756 | 5/1988 | Ross | 433/173 |
| 4,756,689 | 7/1988 | Lundgren | 433/173 |

FOREIGN PATENT DOCUMENTS 1352188  5/1974  United Kingdom ................. 433/173
WO85/02337  6/1985  World Int. Prop. O. .......... 433/174

OTHER PUBLICATIONS

Brånemark, Osseointegrated Implants in the Treatment of the Edentulous Jaw.
Ekstrand, Ruyter: "Implant-Fixed Dental Bridges", Biomaterials 1986, vol. 7, pp. 73–75.
Branemark, "Osseointegration and its Experimental Background", J. of Pros. Dent., V. 50, No. 3, pp. 399–410, Sep. 1983.

Primary Examiner—John J. Wilson
Attorney, Agent, or Firm—White & Case

[57] ABSTRACT

A dental bridge assembly comprises a bridge component cast from a gold alloy having a melting point not greater than 1050° C. and a plurality of sockets of titanium or a titanium alloy cast in place in the bridge component, secured mechanically to the bridge component and adapted to be fastened to anchor elements attached to the jawbone of a patient.

10 Claims, 1 Drawing Sheet

DENTAL BRIDGE AND MANNER FOR PREPARATION

TECHNICAL FIELD

The present invention is related to a dental bridge made of gold alloy and provided with sockets cast into said bridge, through which sockets the bridge will be attached to anchoring elements attached to the jaw of a patient. The object of the invention is to achieve a dental bridge at a lower cost than with previously known bridges, which bridge may be prepared with a simplified procedure and using less details.

STATE OF THE ART

From Adell et al., Int. J. Oral Surg. 10 (1981), page 388 is known a dental implant system wherein a gold cylinder (k), which is attached with a gold screw (1), is intended to be cast into a bridge structure of gold alloy. Zarb and Symington in Proceedings of the Toronto Conference in Clinical Dentistry, J. of Prosthetic Dentistry, vol. 50, No. 2, page 272, have used a gold cylinder which was cast into a dental bridge of silver palladium alloy. Use of sockets which are machined gold details causes high costs for such implant systems.

WO 85/02337 shows a dental implant in which a socket-shaped part 7 made of titanium or other material is attached by a screw joint against a corresponding cavity taken up in a dental bridge. However, it is not suggested to cast said part into the dental bridge.

DESCRIPTION OF THE INVENTION

According to the present invention it has surprisingly been found possible to prepare a dental bridge of the kind referred to initially wherein the sockets comprise a supporting part made of titanium the outer surface of which is provided with retention means for locking the socket against axial movement. It has thus been found that a strong and durable connection between the bridge and the sockets can be obtained without any chemical bond occurring therebetween, thus as is the case in use of gold cylinders. It has been found that sockets of titanium under certain conditions may be destroyed during the process of casting the sockets in. It has however been found that if one, according to a preferred embodiment of the invention, uses a gold alloy with a melting point not exceeding 1050° C. this problem will be avoided. According to a further preferred embodiment of the invention the suPporting parts of the sockets are made of titanium in commercially pure grade or of a titanium alloy comprising titanium, aluminium and vanadinum (e.g. 90:6:4), titanium, aluminium and iron or titanium, aluminium and niobium.

The retention means of the sockets, for locking against axial movement, are preferably in the forms of one or more grooves going around the supporting part thereof. The groove can preferably have the profile of a circle segment. The sockets may further suitably have retention means for prevention of rotation. These may comprise notches in the axial direction in the outer surface of the socket.

For preparing a dental bridge according to the invention sockets of titanium are cast into gold or a gold alloy in a model casting process.

The means for preparing a dental bridge comprises a socket which is characterized in that it has a supporting part made of titanium, the outer surface of which is provided with retention means for locking of the socket against axial movement. The supporting part is preferably made of the above-mentioned titanium alloy. The socket may in addition to the supporting part, which at one end is provided with a supporting surface for bearing against a bearing surface of a spacing element attached to the jaw-bone of a patient, preferably be provided at the opposite end thereof with a tubular thin-walled extension which may form a channel through an impression material on modelling of a prosthetic part, and thereby enable the use of the socket also during the prosthesis building work. Suitably the tubular extension is made in one piece with the supporting part of the socket, and due to this, the socket in its entirety is preferably made of titanium.

The invention is further described with reference to the appended drawings, where:

DESCRIPTION OF EMBODIMENTS

Figure 1:
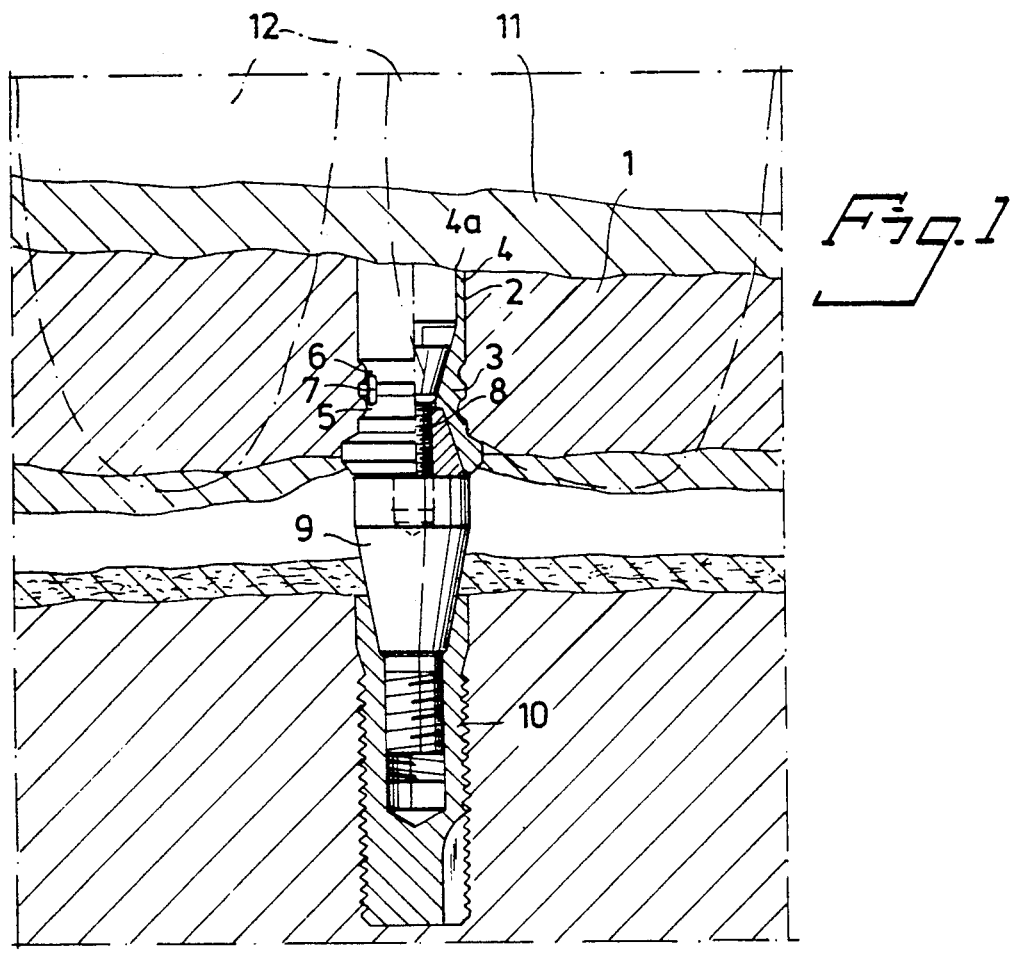
FIG. 1 is a lengthwise section through a dental bridge according to the invention attached via an anchoring device implanted into a jaw.
Figure 2:
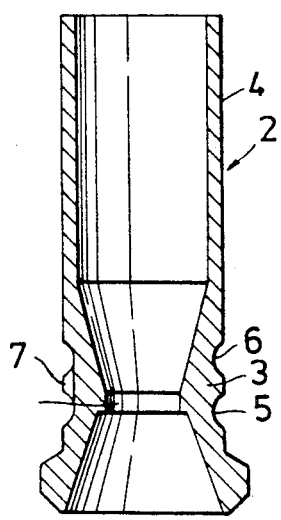
FIG. 2 is a section through a socket according to one embodiment of the means according to the invention.

A dental bridge of gold alloy according to the invention is denoted 1, and is provided with a titanium socket 2 cast thereinto, which socket has a lower supporting part 3 and a tubular extension 4 made in one piece with the supporting part of the socket. In the dental bridge in FIG. 1 the extension is ground down to a suitable length at 4a. On the supporting part two round-going grooves 5 and 6 are arranged as retention means against axial movement. Between said grooves a number of axially directed notches 7 are arranged for retention against rotation. The socket is attached by a screw 8 against a pillar 9, which in turn is screwed into an osseointegrated root element 10. The dental bridge 1 is surrounded by a prosthesis 11 of acrylic material in which false teeth 12 are attached.

Figure 3:
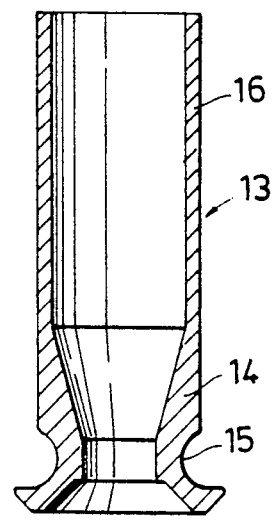
FIG. 3 is a section through a socket according to another embodiment of the means according to the invention.

The socket in FIG. 3 is denoted 13 and has a supporting part 14 with a circular groove 15 serving as retention means against axial movement. At the end of the supporting part of the socket which is to be directed away from the pillar whereon it will be attached, the socket has a tubular extension 16.

The dental bridge according to the invention may be prepared in the following manner:

Bores for root screws 10 are drilled in the jaw-bone, root screws are screwed in and are allowed to osseointegrate in a known manner. After uncovering of the upper ends of the root screws pillars 9 are screwed in, which are allowed to heal in under protection of a healing cap attached over the conical supporting surface thereof. The healing cap is removed and sockets 2 are placed thereon and attached by screws 8. If desired, a plastic impression material may be placed over the sockets for making an impression of the teeth of the opposite jaw, which impression is used by the dental technician in the final preparation of the prosthesis. The ends of the sockets are sealed with a plastic material, whereupon an impression tray filled with plaster is depressed over the sockets and the plaster is allowed to solidify. The seal over the ends of the sockets is removed, the screws 8 are released and the plaster impression is removed. Pillar dummies with conical supporting surfaces similar to the supporting surfaces of the pillars 9 are attached into the sockets by the screws 8 and cast into plaster. The first plaster impression is removed and broken down to release of the sockets 2, alternatively new similar sockets 2 are taken, and the sockets are mounted on the pillar dummies. A bridge structure is modelled of wax or plastic material and, a mould is prepared by pressing the bridge structure into a mould compound and burning the wax or plastic material out in a burning oven. The gold alloy is thereafter cast into the mould to formation of a dental bridge 1 wherein the sockets are cast in and mechanically secured.

An example of a suitable gold alloy is an alloy denoted DR 400 of the Ugdo brand, which is a so called class 4 gold, i.e. hard gold. Said alloy has the composition Au 720, Pt 30, Ag 140, Cu 101, Zn 9 and the melting temperature 885–895° C. Another suitable alloy is "Sj/ödings C-guld", which is a so called class 3 gold i.e. a somewhat softer gold which has the composition Au 765, Pt 29.5, Ir 0.5, Ag 85, Cu 115, Zn 5 and the melting temperature 880–945° C. In both cases the alloy is heated suitably to about 100° over the melting temperature. The mould is temperated suitably to maximum about 675° C.

I claim:

1. A dental assembly comprising a bridge component and a plurality of sockets that are adapted to be attached to anchoring elements affixed to a patient's jawbone, each socket being of a material selected from the group consisting of titanium and an alloy of titanium, having a retention portion embedded in the bridge component that is shaped to lock the socket mechanically against axial movement, and being cast in place in the bridge component to form the mechanical lock, and the bridge component being of a gold alloy having a melting point not greater than 1050° C.

2. A dental assembly according to claim 1 wherein the material of each socket is titanium of a commercially pure grade.

3. A dental assembly according to claim 1 wherein the material of each socket is a titanium alloy containing titanium, aluminum and vanadium.

4. A dental assembly according to claim 1 wherein the material of each socket is a titanium alloy containing titanium, aluminum and iron.

5. A dental assembly according to claim 1 wherein the material of each socket is a titanium alloy containing titanium, aluminum and niobium.

6. A dental assembly according to any of claims 1 to 5 wherein the retention portion has at least one peripheral groove.

7. A dental assembly according to claim 1, wherein the socket includes means for locking the socket mechanically against rotation in the bridge component.

8. A method of preparing a dental bridge assembly comprising the steps of:
   (a) providing a plurality of sockets that are adapted to be attached to anchoring elements affixed to a patient's jawbone, the sockets being selected from the group consisting of titanium and an alloy of titanium and having a retention portion on the outer surface which, when embedded in a bridge material, prevents axial movement of the socket;
   (b) positioning the retention portions of the sockets in a bridge making mold; and
   (c) casting a gold alloy, having a melting point not exceeding 1050° C. into the mold to solidify around the retention portions and form a dental bridge, the embedded sockets thereby being secured against axial movement.

9. A method according to claim 8, wherein the gold alloy is heated to a temperature of about 100° C. over the melting temperature when cast.

10. A method according to claim 9, wherein a gold alloy is selected having a melting temperature within a range of about 880–945° C.

* * * * *